(12) United States Patent
Nagel et al.

(10) Patent No.: US 7,723,088 B2
(45) Date of Patent: May 25, 2010

(54) DNA SEQUENCES INVOLVED IN PRENYLFLAVONOID BIOSYNTHESIS IN HOPS AND THEIR USE IN MODIFYING PRENYLFLAVONOID PRODUCTION IN PLANTS

(76) Inventors: Jana Nagel, Hardenbergstrrasse 3, Halle (DE) 06114; Jonathan Page, 305 Main Street, Saskatoon, SK (CA) S7N 0B61

( * ) Notice: Subject to any disclaimer, the term of this patent is extended or adjusted under 35 U.S.C. 154(b) by 0 days.

(21) Appl. No.: 12/066,004

(22) PCT Filed: Sep. 6, 2006

(86) PCT No.: PCT/CA2006/001463

§ 371 (c)(1),
(2), (4) Date: Jun. 17, 2008

(87) PCT Pub. No.: WO2007/028239

PCT Pub. Date: Mar. 15, 2007

(65) Prior Publication Data

US 2009/0222946 A1   Sep. 3, 2009

Related U.S. Application Data

(60) Provisional application No. 60/713,751, filed on Sep. 6, 2005.

(51) Int. Cl.
*C12N 9/00* (2006.01)
*C12N 9/10* (2006.01)

(52) U.S. Cl. .................... 435/183; 435/193
(58) Field of Classification Search .................. None
See application file for complete search history.

(56) References Cited

OTHER PUBLICATIONS

Wu et al. (Journal of Bioscience or Bioengineering, 96:119-128, 2003).*

Ounaroom et al., NCBI GenBank Sequence Accession No. AY268893, Published Dec. 16, 2003.*

Wu, S. et al Two O-methyltransferases isolated from flower petals of Rosa chinensis var. spontanea involved in scent biosynthesis J. Biosci Bioeng 2003 Vo. 96, No. 2 pp. 119-128 ISSN 1389-1723.

Stevens, J.F. and Page J.E. Xanthohumol and related prenylflavonoids from hops and beer: to your good health Phytochemistry May 2004 vol. 65 No. 10, pp. 1317-1330 ISSN 0031-9422.

Ibrahim R.K. et al Plant O-methyltransferases: molecular analysis, common signature and classification Plant Mol Biol. Jan. 1998 vol. 36 No. 1 pp. 1-10.

Joshi, C.P. and Chiang, V.L. Conserved sequences motifs in plant S-adenosyl-L-methionine dependent methyltransferases. Plant Mol Biol. Jul. 1998. vol. 37, No. 4 pp. 663-674.

Stevens, J.F. et al. Prenylflavonoids from Humulus Lupulus. Phytochemistry. 1997, vol. 44, No. 8, pp. 1575-1585.

Jiang, H. et al. Metabolic Engineering of the Phenylpropanoid Pathway in *Saccharomyces cerevisiae*. Applied and Environmental Microbiology, Jun. 2005, p. 2962-2969.

Matousek, J. et al. Cloning and Characterisation of chs-specific DNA and cDNA sequences from hop (Humulus lupulus L.). Plant Science 162 (2002) 1007-1018.

Maxwell, C.A. et al. Molecular Characterization and Expression of alfalfa isoliquiritigenin 2'-0-methyltransferase, an enzyme specifically involved in the biosynthesis of an inducer of Rhizobium meliloti nodulation genes. The Plant Journal (1993) 4 (6), 971-981.

Zubieta, C. et al. Structures of two natural product methyltransferases reveal the basis for substrate specificity in plant 0-methyltransferases. Nature structural biology, vol. 8 No. 3, Mar. 2001.

* cited by examiner

*Primary Examiner*—Vinod Kumar
(74) *Attorney, Agent, or Firm*—Michael R. Williams; Ade & Company Inc.

(57) ABSTRACT

The isolation and identification of two O-methyltransferases from the hops plant (*Humulus lupulus* L.), designated as OMT1 (SEQ ID NO. 1) and OMT2 (SEQ ID NO. 3) is described.

2 Claims, 4 Drawing Sheets

Figure 4. Prenylflavonoid biosynthesis in hops.

SEQUENCE LISTING

<160> NUMBER OF SEQ ID NOS: 4

<210> SEQ ID NO 1
<211> LENGTH: 1240
<212> TYPE: DNA
<213> ORGANISM: Humulus lupulus

<400> SEQUENCE: 1

```
ggacacaatt caatctattt tacccaaaaa ataactaaga aagaccaata tggaatctct      60
aagaggccaa gaacagatat ggcaactcat gttcagcttt gtcgactcca tggccttgaa     120
atgcgccatc gagcttcgca ttgctgacat cattcactct catggcaaac ctataactct     180
ctcccaaata gcttctggca ttcgatcaaa ctccaactcc tccatatctc cgaatattcc     240
ttacctctct cgcatcatga gatttcttgt tcgaaagaat atcttcactg aacatcaaga     300
agataatgat gaggtgatct cattgtacgg gctaagtgat agctcgagat ggctgttgcg     360
ggattttaag tcaagcctgg ctcccatggt gctcatgcag actcatccat tgtcgatggc     420
ggtgtggcat ttccttgagg attatgtgag aaacagcagc aacactttcg aaaaggctca     480
cggttgtaac atttgggagt tttcctcagc caatccagat ttcaacaaga tcttcaacaa     540
tgccatggcg agtattgtgc caatatacat ggggctgtg ctttcaagtt ataaggatgg     600
tcttggttgt attaaaggaa cagtggtgga cgttggggt ggtacgggcg ctccatatc      660
agagcttatg aaatattatc caaacatcaa agggattaac tttgacctgc acatgtgat      720
tgccacagca ccggcattgg atggtgttac ccatattagt ggtgacatat tcgagtcaat     780
tcctagtgct gatgcggttt taatgaaggg tgtactacat tgcttcagcg atgaaaaatg     840
tgtaaaagta ttgagaaatt gtcgaaaagc aataacagac aaaaagaatg ggaagattat     900
catttggag attgtgttgg acccaaccag caatcaaata tttgacgaga ctcgaatggt     960
gtacgattta ttgattccay tctttagtgg tggaaaagag agaactgagc ttgaatggaa    1020
aaggctatta aacgaggctg gttttacttc tatcaaaatc accaaaattc aattatacc    1080
tgctattatt gaggcctttc tagtgtgaca acatcgatct atctatatat ataaaacta    1140
ggttatgttg ctttcaacaa taagttccct atgtactgtt acggttatgt atggtttgct    1200
gtgattaata taatatgttg gcaaaaaaaa aaaaaaaaa                           1240
```

<210> SEQ ID NO 2
<211> LENGTH: 352
<212> TYPE: PRT
<213> ORGANISM: Humulus lupulus
<220> FEATURE:
<221> NAME/KEY: misc_feature
<222> LOCATION: (311)..(311)
<223> OTHER INFORMATION: Xaa can be any naturally occurring amino acid

<400> SEQUENCE: 2

```
Met Glu Ser Leu Arg Gly Gln Glu Gln Ile Trp Gln Leu Met Phe Ser
1               5                   10                  15

Phe Val Asp Ser Met Ala Leu Lys Cys Ala Ile Glu Leu Arg Ile Ala
            20                  25                  30

Asp Ile Ile His Ser His Gly Lys Pro Ile Thr Leu Ser Gln Ile Ala
        35                  40                  45

Ser Gly Ile Arg Ser Asn Ser Asn Ser Ile Ser Pro Asn Ile Pro
    50                  55                  60

Tyr Leu Ser Arg Ile Met Arg Phe Leu Val Arg Lys Asn Ile Phe Thr
```

-continued

```
            65                  70                  75                  80
Glu His Gln Glu Asp Asn Asp Glu Val Ile Ser Leu Tyr Gly Leu Ser
                    85                  90                  95
Asp Ser Ser Arg Trp Leu Leu Arg Asp Phe Lys Ser Ser Leu Ala Pro
                100                 105                 110
Met Val Leu Met Gln Thr His Pro Leu Ser Met Ala Val Trp His Phe
            115                 120                 125
Leu Glu Asp Tyr Val Arg Asn Ser Ser Asn Thr Phe Glu Lys Ala His
        130                 135                 140
Gly Cys Asn Ile Trp Glu Phe Ser Ser Ala Asn Pro Asp Phe Asn Lys
145                 150                 155                 160
Ile Phe Asn Asn Ala Met Ala Ser Ile Val Pro Ile Tyr Met Gly Ala
                165                 170                 175
Val Leu Ser Ser Tyr Lys Asp Gly Leu Gly Cys Ile Lys Gly Thr Val
                180                 185                 190
Val Asp Val Gly Gly Gly Thr Gly Gly Ser Ile Ser Glu Leu Met Lys
            195                 200                 205
Tyr Tyr Pro Asn Ile Lys Gly Ile Asn Phe Asp Leu Pro His Val Ile
        210                 215                 220
Ala Thr Ala Pro Ala Leu Asp Gly Val Thr His Ile Ser Gly Asp Ile
225                 230                 235                 240
Phe Glu Ser Ile Pro Ser Ala Asp Ala Val Leu Met Lys Gly Val Leu
                245                 250                 255
His Cys Phe Ser Asp Glu Lys Cys Val Lys Val Leu Arg Asn Cys Arg
                260                 265                 270
Lys Ala Ile Thr Asp Lys Lys Asn Gly Lys Ile Ile Leu Glu Ile
            275                 280                 285
Val Leu Asp Pro Thr Ser Asn Gln Ile Phe Asp Glu Thr Arg Met Val
        290                 295                 300
Tyr Asp Leu Leu Ile Pro Xaa Phe Ser Gly Gly Lys Glu Arg Thr Glu
305                 310                 315                 320
Leu Glu Trp Lys Arg Leu Leu Asn Glu Ala Gly Phe Thr Ser Ile Lys
                325                 330                 335
Ile Thr Lys Ile Pro Ile Ile Pro Ala Ile Ile Glu Ala Phe Leu Val
            340                 345                 350
```

<210> SEQ ID NO 3
<211> LENGTH: 1312
<212> TYPE: DNA
<213> ORGANISM: Humulus lupulus

<400> SEQUENCE: 3

| | | | | | |
|---|---|---|---|---|---|
| atcaatcatt | cgacctttct | ataacataaa | agaaaaaga | aaaaaagtg | agattagtgt | 60 |
| aaatggagtt | ggcacggaat | gatcaaaccg | aggcagctct | aagaggtgaa | gcgaacgtat | 120 |
| ggaaaagcat | taatggaata | gcagatttca | tggtcatgaa | atgcgcctta | gagttgagaa | 180 |
| tccctgatat | cgtacactcg | cactccgccc | caatcacttt | ggcccaaatt | gcttcttctg | 240 |
| ttccagattc | tccctctctg | aacctctcct | acctatctcg | catcatgcgt | ctacttgtac | 300 |
| gtcgtaaagt | attctctcaa | cacaaatcac | tagacggtga | agaagttctc | tacgggccta | 360 |
| ctcactcatc | taggttgctc | ttaagcaaaa | ctacgttgcc | ggatcaggta | actttggctc | 420 |
| cgtttgttgc | attcatgacc | catccctact | tgtcggctcc | atggagctgc | ttggccaggt | 480 |
| gtgtcaaaga | aggcggcaac | ggttttgaga | tggtccacgg | cggccgccaa | ttatgggact | 540 |

```
tgtctccagg gaatccggag ttcaacaagg ttttcaacga tggcatggcg agcacggcca    600
gaataacaac gatggcaatt ttgtccgaat acagagatgc tttttgtggg atctgttctt    660
tggtcgacgt cggtggtgag tttggcggct caatatctgc gattgtgaaa tctcatccgc    720
acataaaagg catcaactat gatctacccc atgttgtcgc accgctcca acgtacaccg     780 gactagtgtc ccatgttggt ggtaacatgt ttgaatggat ccccactgcc gttgcagttt    840
tcatgaagtg gatacttcac gattgggccg atgaagattg tgtgaagatc ttgaaaaatt    900
gtagaagagc aatgcctgag aagggtggaa aattatcat agttgacata gttttggagc     960
cagagggcaa tgggttattt gatgatgcag ctgtgatgct cgatattgca ctaatggcac    1020
taacacgtgg aaaggagaga accgagaagg agtggaagag ggtgttggaa gaaggaggtt    1080
tccctcgcta ccaaatcctc aaaattccag ctttaacatc tgtcattgaa gcctatccac    1140
aatgatcatc actgtatacc taccctatta tgatgttcta gtagttcata gacactttct    1200
taaaggtgca atatggatga ataagttaat tatatttaaa ataatatgat atctcctata    1260
tataataaat ggctatggaa tggaaaattg atagtttaat ggaaaaaaaa aa             1312
```

<210> SEQ ID NO 4
<211> LENGTH: 360
<212> TYPE: PRT
<213> ORGANISM: Humulus lupulus

<400> SEQUENCE: 4

```
Met Glu Leu Ala Arg Asn Asp Gln Thr Glu Ala Ala Leu Arg Gly Glu
1               5                   10                  15

Ala Asn Val Trp Lys Ser Ile Asn Gly Ile Ala Asp Phe Met Val Met
                20                  25                  30

Lys Cys Ala Leu Glu Leu Arg Ile Pro Asp Ile Val His Ser His Ser
            35                  40                  45

Ala Pro Ile Thr Leu Ala Gln Ile Ala Ser Ser Val Pro Asp Ser Pro
        50                  55                  60

Ser Leu Asn Leu Ser Tyr Leu Ser Arg Ile Met Arg Leu Leu Val Arg
65                  70                  75                  80

Arg Lys Ile Phe Ser Gln His Lys Ser Leu Asp Gly Glu Glu Val Leu
                85                  90                  95

Tyr Gly Pro Thr His Ser Ser Arg Leu Leu Leu Ser Lys Thr Thr Leu
            100                 105                 110

Pro Asp Gln Val Thr Leu Ala Pro Phe Val Ala Phe Met Thr His Pro
        115                 120                 125

Tyr Leu Ser Ala Pro Trp Ser Cys Leu Ala Arg Cys Val Lys Glu Gly
    130                 135                 140

Gly Asn Gly Phe Glu Met Val His Gly Gly Arg Gln Leu Trp Asp Leu
145                 150                 155                 160

Ser Pro Gly Asn Pro Glu Phe Asn Lys Val Phe Asn Asp Gly Met Ala
                165                 170                 175

Ser Thr Ala Arg Ile Thr Thr Met Ala Ile Leu Ser Glu Tyr Arg Asp
            180                 185                 190

Val Phe Cys Gly Ile Cys Ser Leu Val Asp Val Gly Gly Glu Phe Gly
        195                 200                 205

Gly Ser Ile Ser Ala Ile Val Lys Ser His Pro His Ile Lys Gly Ile
    210                 215                 220

Asn Tyr Asp Leu Pro His Val Val Ala Thr Ala Pro Thr Tyr Thr Gly
225                 230                 235                 240
```

-continued

Leu Val Ser His Val Gly Gly Asn Met Phe Glu Trp Ile Pro Thr Ala
            245                 250                 255

Val Ala Val Phe Met Lys Trp Ile Leu His Asp Trp Ala Asp Glu Asp
            260                 265                 270

Cys Val Lys Ile Leu Lys Asn Cys Arg Arg Ala Met Pro Glu Lys Gly
            275                 280                 285

Gly Lys Ile Ile Ile Val Asp Ile Val Leu Glu Pro Glu Gly Asn Gly
            290                 295                 300

Leu Phe Asp Asp Ala Ala Val Met Leu Asp Ile Ala Leu Met Ala Leu
305                 310                 315                 320

Thr Arg Gly Lys Glu Arg Thr Glu Lys Glu Trp Lys Arg Val Leu Glu
            325                 330                 335

Glu Gly Gly Phe Pro Arg Tyr Gln Ile Leu Lys Ile Pro Ala Leu Thr
            340                 345                 350

Ser Val Ile Glu Ala Tyr Pro Gln
            355                 360

DNA SEQUENCES INVOLVED IN PRENYLFLAVONOID BIOSYNTHESIS IN HOPS AND THEIR USE IN MODIFYING PRENYLFLAVONOID PRODUCTION IN PLANTS

PRIOR APPLICATION INFORMATION

This application claims the benefit of U.S. Provisional Patent Application 60/713,751, filed Sep. 6, 2005.

BACKGROUND OF THE INVENTION

The hops plant (*Humulus lupulus* L.) is an important ingredient of beer, contributing both taste and nutraceutical properties. The latter are mainly due to the presence of prenylflavonoids such as xanthohumol.

Xanthohumol (1-[2,4-dihydroxy-6-methoxy-3-(3-methylbut-2-enyl)phenyl]-3-(4-hydroxyphenyl)-prop-2-en-1-one) is a prenylflavonoid found only in the hops. Xanthohumol possesses a range of biological activities, which include antioxidation and cancer chemoprevention via phase 2 protein induction (Stevens and Page, 2004). Increasing the levels of xanthohumol may lead to hops varieties that have enhanced health-promoting properties. Knowledge of the genes encoding the enzymes of xanthohumol biosynthesis may allow production of xanthohumol in alternative host organisms, such as bacteria.

8-Prenylnaringenin (5,7-dihydroxy-2-(4-hydroxyphenyl)-8-(3-methylbut-2-enyl)chroman-4-one) is formed by the isomerization of desmethylxanthohumol (a precursor of xanthohumol, see below) to its corresponding flavanone. 8-Prenylnaringenin is the most potent phytoestrogen thus far identified. It therefore has potential as a selective estrogen receptor modulator (SERM) for treatment of osteoporosis and other menopausal/post-menopausal conditions.

Figure 1:
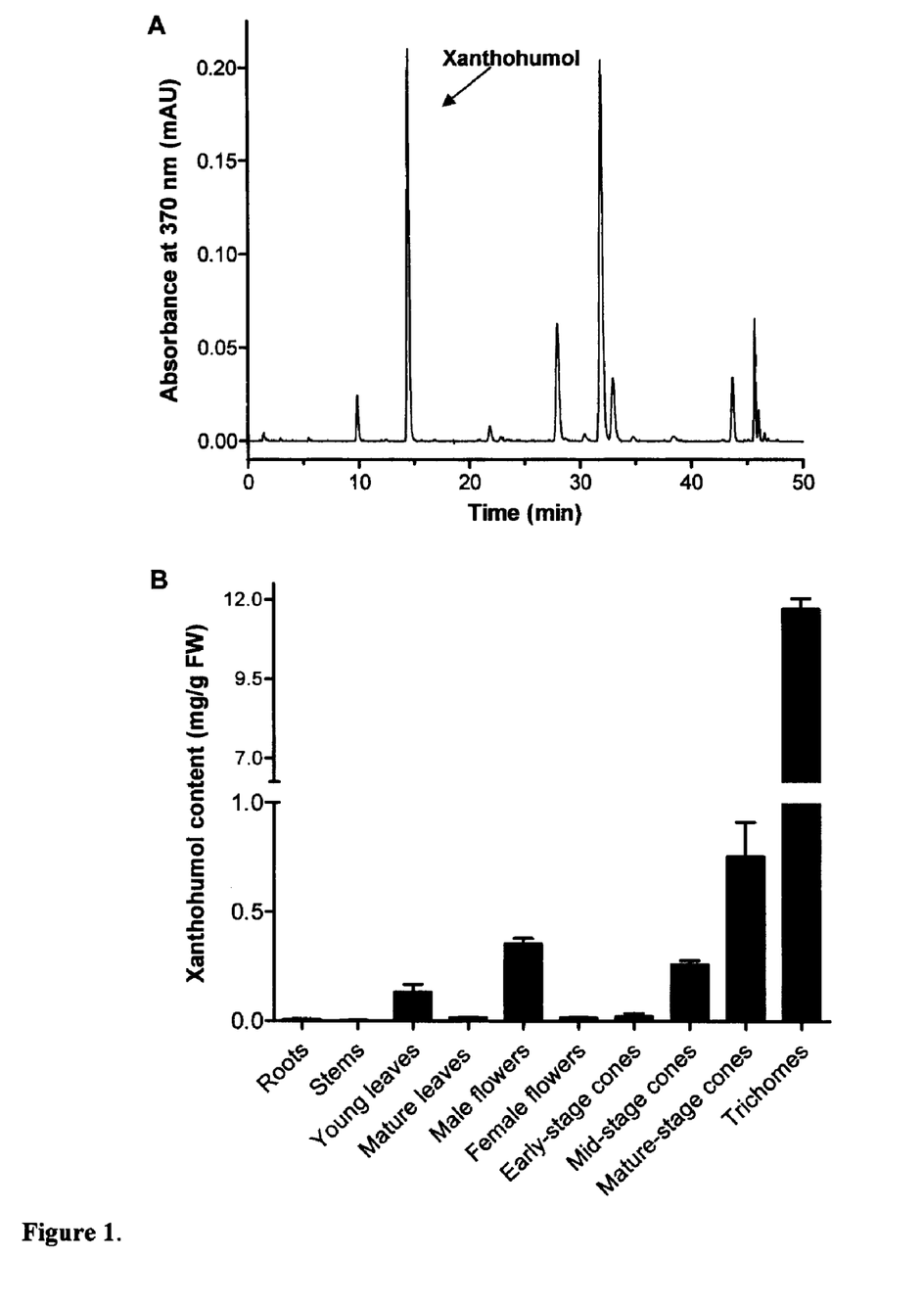
FIG. 1. HPLC analysis of xanthohumol levels in different hop tissues. Xanthohumol is found primarily in lupulin glands of hop. (A). Reversed-phase HPLC chromatogram (detection at 370 nm) of lupulin glands from H. lupulus cv. 'Taurus' showing peak corresponding to xanthohumol. (B). Xanthohumol levels in different hop tissues as determined by quantitative HPLC analysis.
Figure 2:
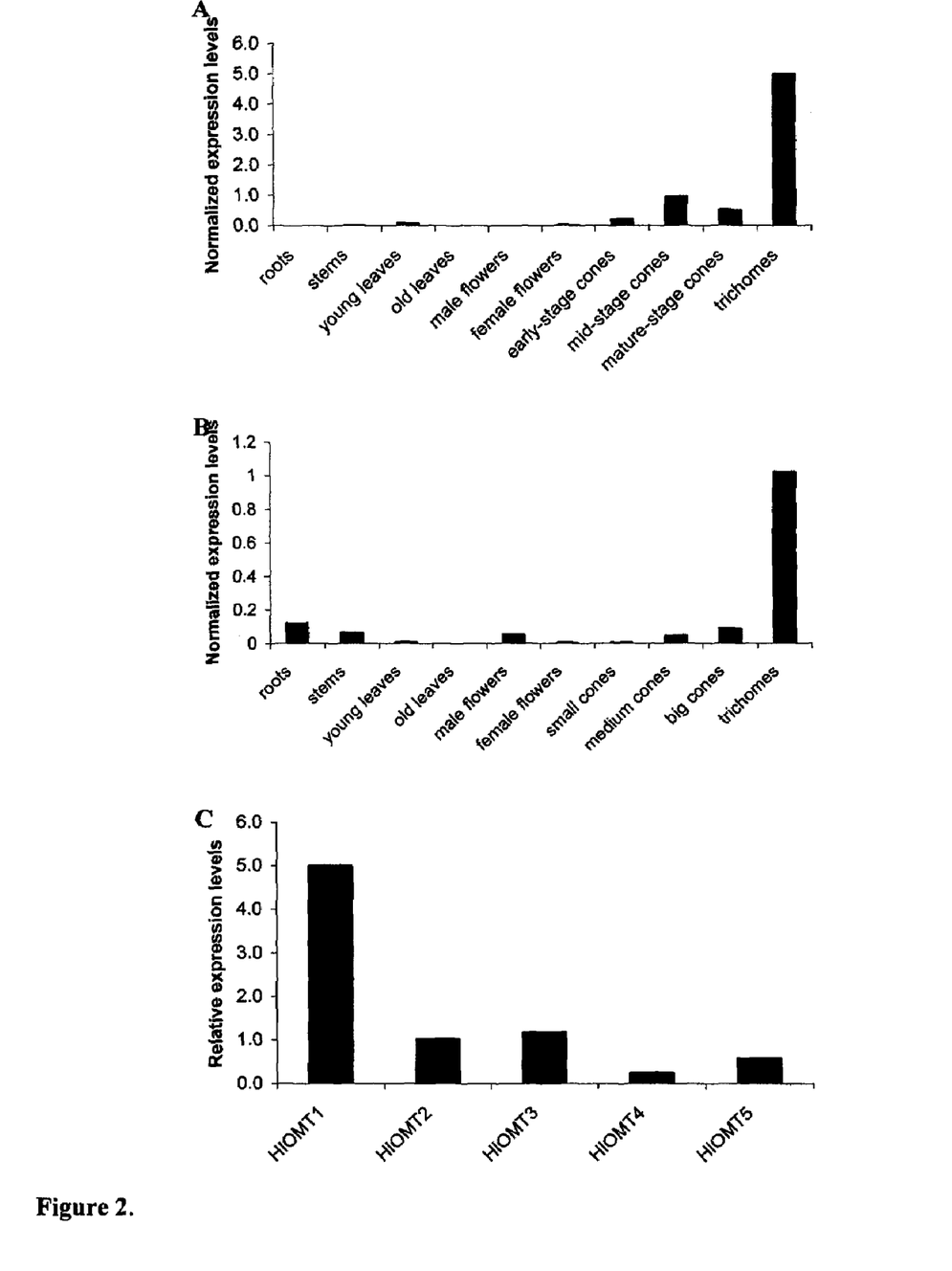
FIG. 2. Quantitative real-time PCR analysis of the gene expression of HlOMT1 and HlOMT2 in different hop tissues, and a comparison of the expression of five different hop OMTs in lupulin glands (trichomes). Gene expression of hop O-methyltransferases as measured by quantitative real-time PCR. (A) Expression of HlOMT1 in different hop tissues relative to the expression of glyceraldehyde-3-phosphate dehydrogenase (GAPDH). (B) Expression of HlOMT2 in different hop tissues relative to the expression of GAPDH. (C) Expression of five different OMTs from hop in lupulin glands relative to the expression of HlOMT2.
Figure 3:
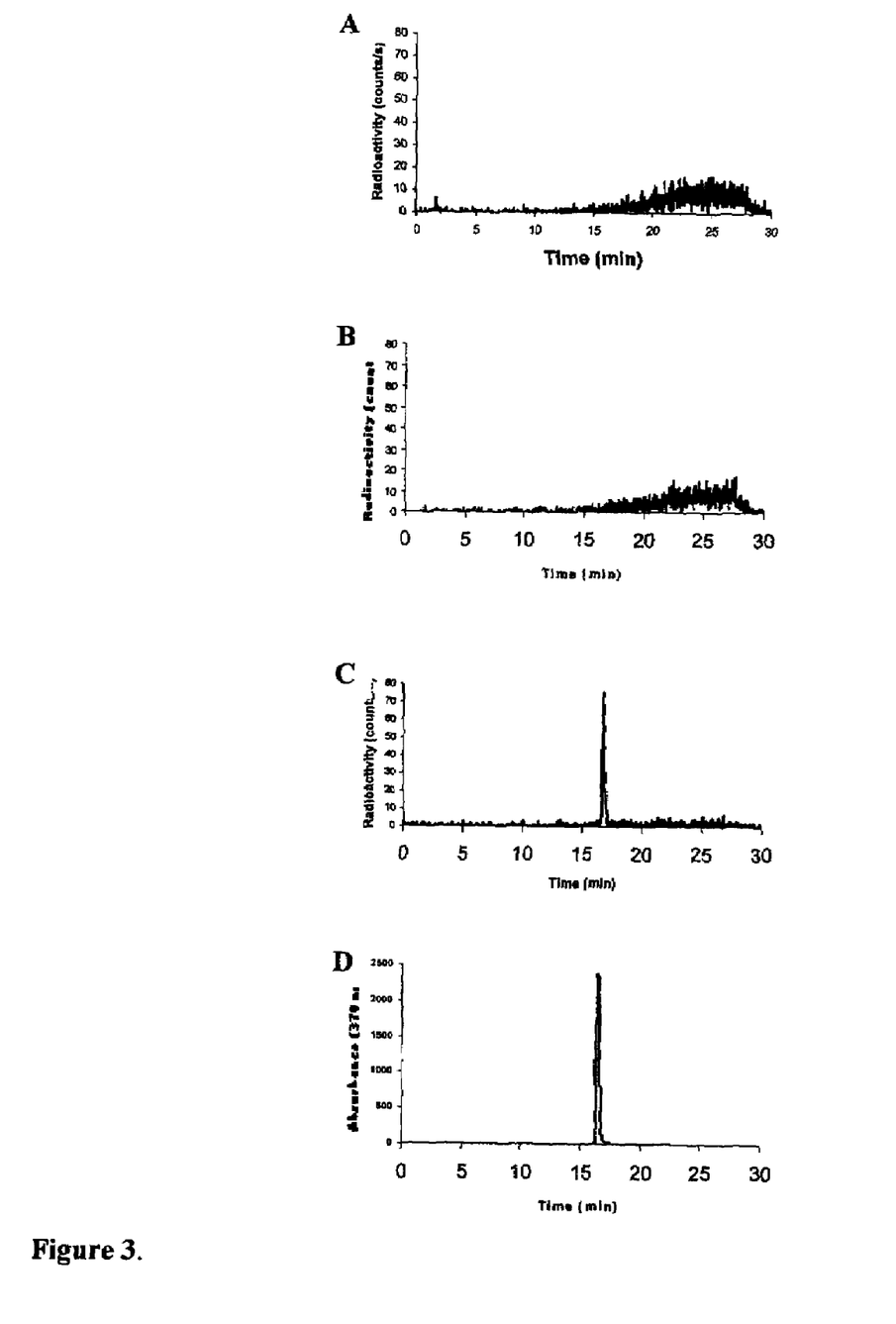
FIG. 3. Enzymatic activity of HlOMT1 showing that this enzyme methylates desmethylxanthohumol to produce xanthohumol. HlOMT1 methylates desmethylxanthohumol to form xanthohumol. Recombinant HlOMT1 was expressed in insect cells and crude cell lysate used for enzymatic assay. (A) Radio-HPLC analysis of reaction products from empty vector control lysate incubated with $^{14}$C-SAM and desmethylxanthohumol. (B) Radio-HPLC analysis of reaction products from HlOMT1 lysate incubated with $^{14}$C-SAM. (C) Radio-HPLC analysis of reaction products HlOMT1 lysate incubated with $^{14}$C-SAM and desmethylxanthohumol showing that xanthohumol is formed (D) Reversed-phase HPLC analysis of authentic xanthohumol.
Figure 4:
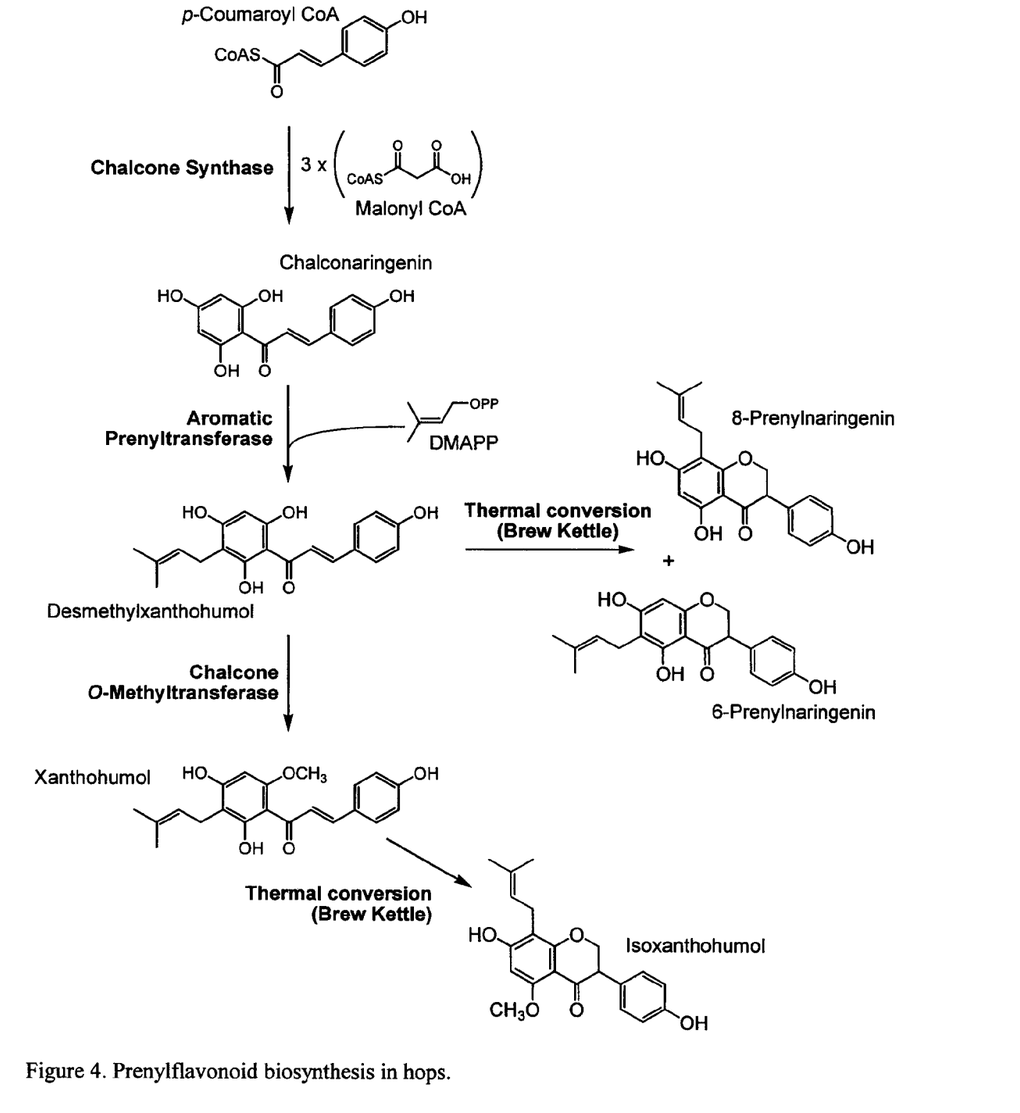
FIG. 4. Prenylflavonoid biosynthesis pathway.

As seen in the reactions illustrated in FIG. 4, the first step in prenylflavonoid biosynthesis is the condensation of p-coumaroyl CoA with three molecules of malonyl CoA to give chalconaringenin (also called naringenin chalcone), a reaction catalyzed by chalcone synthase (CHS, E.C. 2.3.1.74). This step is not unique to prenylflavonoid biosynthesis and chalcone synthase is ubiquitous in plants.

A chalcone synthase gene, chs-H1, was cloned from hops and found to be part of a multigene family consisting of at least six members (Matousek et al., 2002). Prenylation of the A ring of chalconaringenin with dimethylallyl diphosphate (DMAPP) yields desmethylxanthohumol, which is subsequently methylated at the 6'-hydroxyl group to form xanthohumol. Although the order of these two reactions is not clear, the detection of desmethylxanthohumol in hops (Stevens et al., 1997) suggests that prenylation occurs before methylation (and FIG. 4 shows this order). Desmethylxanthohumol isomerizes to 6- and 8-prenylnaringenin during beer brewing.

The prenyltransferase catalyzing desmethylxanthohumol formation has not been cloned or characterized. The O-methylation step, whether it proceeds via desmethylxanthohumol or chalconaringenin, has also not been elucidated in hops. It seems likely that the hops desmethylxanthohumol O-methyltransferase or chalconaringenin O-methyltransferase have similar properties to other plant OMTs such as chalcone O-methyltransferase (ChOMT) from *Medicago sativa* L. in that they use S-adenosyl methionine (SAM or AdoMet) as a methyl donor (Maxwell et al. 1993; Zubieta et al. 2001).

Enhanced production of xanthohumol or other prenylflavonoids such as desmethylxanthohumol (as a precursor of 8-prenylnaringenin) could be accomplished though breeding and selection programs as well as genetic engineering with the use of known genes in the flavonoid pathway.

Chalcones readily isomerize to form their corresponding flavanones via the action of chalcone isomerase. For example, chalconaringenin, the tetrahydroxychalcone precursor of xanthohumol, isomerizes to form (2S)-naringenin. This isomerization also occurs non-enzymatically to yield (2R)- and (2S)-naringenin. Similarly desmethylxanthohumol is isomerized during the beer brewing process to form 6- and 8-prenylanringenin, and xanthohumol isomerizes to isoxanthohumol, albeit at a slower rate.

Methylation of the 6' hydroxyl group of the chalcone A-ring by an O-methyltransferase enzyme slows down the rate of isomerization to the flavanone due to chelation of the remaining free hydroxyl group with the nearby keto functionality. This methylation step is therefore important for two reasons: (1) efficient methylation of either chalconaringenin or desmethylxanthohumol ensures the formation of xanthohumol rather than their corresponding flavanones, (2) prevention of this specific methylation would lead to the accumulation of desmethylxanthohumol at the expense of xanthohumol, which could therefore be converted to 6- and 8-prenylnaringenin. Hops plants containing high amounts of desmethylxanthohumol could be used as sources for the semi-synthesis of 6- and 8-prenylnaringenin, which may be valuable in the pharmaceutical industry.

SUMMARY OF THE INVENTION

According to the invention, we have discovered two genes encoding chalcone O-methyltransferase enzymes from hops.

These genes can be used to create, through breeding, selection or genetic engineering, hops plants that overproduce xanthohumol, or contain reduced xanthohumol/increased desmethylxanthohumol levels. The two genes have been isolated, sequenced and tested to show this biochemical activity.

According to a first aspect of the invention, there is provided a purified or isolated O-methyltransferase comprising at least 85% identity to an amino acid sequence as set forth in SEQ ID No. 2 or SEQ ID No. 4.

According to a second aspect of the invention, there is provided an isolated or purified DNA molecule comprising or having at least 85%, identity to SEQ ID No. 1 or SEQ ID No. 3.

According to a third aspect of the invention, there is provided a DNA molecule comprising at least 85% identity to a DNA molecule deduced from the amino acid sequence as set forth in SEQ ID No. 2 or SEQ ID No. 4.

According to a fourth aspect of the invention, there is provided a method of increasing xanthohumol levels in a hops plant comprising increasing levels of an O-methyltransferase comprising at least 85% identity to an amino acid sequence as set forth in SEQ ID No. 2 or SEQ ID No. 4.

According to a fifth aspect of the invention, there is provided a method of increasing prenylflavonoid levels in a plant comprising increasing levels of an O-methyltransferase comprising at least 85% identity to an amino acid sequence as set forth in SEQ ID No. 2 or SEQ ID No. 4.

According to a sixth aspect of the invention, there is provided a method of increasing desmethylxanthohumol in a plant comprising introducing an antisense or RNAi probe corresponding to a nucleotide sequence complementary to a region of SEQ ID NO: 1 or SEQ ID NO: 3 into a plant of interest, thereby reducing xanthohumol biosynthesis so that desmethylxanthohumol accumulates.

DETAILED DESCRIPTION OF THE INVENTION

Described herein is the isolation and identification of two O-methyltransferases from the hops plant (Humulus lupulus L.), designated as OMT1 (SEQ ID NO. 1) and OMT2 (SEQ ID NO. 3).

Hop cones typically contain 0.1-1% (w/w) xanthohumol and also contain large amounts of alpha-acids, with some high yielding cultivars containing 15-20% (w/w) of these compounds. Given that the biosynthesis of alpha-acids resembles xanthohumol biosynthesis, overexpression or increased expression of OMT1 or OMT2 compared to a wild-type control which has normal levels of OMT1 or OMT2 for the same variety grown under similar or identical conditions will result in increased levels of xanthohumol, for example, 1-20%, 2-20%, 5-20%, 10-20%, 15-20%, 1-15%, 1-10%, 2-15%, 2-10%, 5-15%, or 10-15% (w/w).

Accordingly, in one aspect of the invention, there is provided a method of increasing xanthohumol levels in a hops plant comprising increasing OMT1 or OMT2 levels in a hop plant and recovering hop cones from said plant. The modified hop plant preferably has increased OMT1 or OMT2 levels compared to an unmodified hop plant of a corresponding variety grown under same or similar conditions. The corresponding variety may be the same variety or a similar variety as the modified hops plant. The OMT1 or OMT2 levels may be increased by transforming the hops plant with an expression system comprising a DNA molecule having at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identical to SEQ ID No. 1 or SEQ ID No. 3 or a DNA molecule at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identical to a DNA molecule deduced from the amino acid sequence as set forth in SEQ ID No. 2 or SEQ ID No. 4. As will be appreciated by one of skill in the art, the expression system may include the native OMT1 or OMT2 promoter and terminator sequences or the expression system may be engineered to include for example a strong promoter or inducible promoter that is functional in hops. It is noted that examples of such promoters are well-known to one of skill in the art.

As can be seen in Table 2, both OMT1 and OMT2 are capable of using desmethylxanthohumol as a substrate. As such, as discussed above, homologs of either enzyme may be used to increase xanthohumol levels in hops as discussed above.

In other embodiments, there is provided an isolated or purified DNA molecule comprising or having at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identity to SEQ ID No. 1 or SEQ ID No. 3 or a DNA molecule at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identity to a DNA molecule deduced from the amino acid sequence as set forth in SEQ ID No. 2 or SEQ ID No. 4.

As will be appreciated by one of skill in the art, the length of the DNA molecule described above will depend on the intended use. For example, if the intended use is as a primer or probe for example for PCR amplification or for screening a library, the length of the DNA molecule will be less than the full length sequence, for example, 15-50 nucleotides. In these embodiments, the primers or probes may be substantially identical to a highly conserved region of the DNA sequence or may be substantially identical to either the 5' or 3' end of the DNA sequence. In some cases, these primers or probes may use universal bases in some positions so as to be 'substantially identical' but still provide flexibility in sequence recognition. It is of note that suitable primer and probe hybridization conditions are well known in the art.

As will be understood by one of skill in the art, in all instances wherein reference is made to 'increasing', 'decreasing', 'modulating' or the like, it refers to comparison to a similar variety grown under similar conditions but without the modification resulting in the increase, decrease or modulation. In some cases, this may be an untransformed control, a mock transformed control, or a vector-transformed control.

In other embodiments, wherein the DNA molecule is used in an expression system to provide enzymatic function to a plant of interest as discussed below, the DNA molecule may have at least 85% identity as discussed above over the entire length of the DNA molecule.

In other embodiments, there is provided a purified or isolated peptide comprising or having at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identity to an amino acid sequence as set forth in SEQ ID No. 2 or SEQ ID No. 4.

In another aspect of the invention, there is provided a method of increasing prenylflavonoid levels in a plant comprising increasing OMT1 or OMT2 levels in a plant. The plant preferably has increased OMT1 or OMT2 levels compared to an unmodified plant of a corresponding variety grown under same or similar conditions. The corresponding variety may be the same variety or a similar variety as the modified plant. The OMT1 or OMT2 levels may be increased by transforming the plant with an expression system comprising a DNA molecule having at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identical to SEQ ID No. 1 or SEQ ID No. 3 or a DNA molecule at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identical to a DNA molecule deduced from the amino acid sequence as set forth in SEQ ID No. 2 or SEQ ID No. 4. As will be appreciated by one of skill in the art, the expression system may include promoter and terminator sequences functional in said plant for example a strong promoter or inducible promoter. It is noted that examples of such promoters are well-known to one of skill in the art.

In a preferred embodiment, the plant is a hop plant.

As can be seen in Table 2, OMT1 has been shown to methylate xanthogalenol and desmethylxanthohumol.

OMT2 has been shown to methylate chalconaringenin, desmethylxanthohumol, xanthohumol, isoliquiritigenin, resveratrol, butein, 2',4-dihydroxychalcone, guaiacol, genistein, eugenol, orcinol, catechol, and resorcinol.

It is of note that chalconaringenin for example is widespread in plants and is an intermediate in flavonoid biosynthesis. For example, some varieties of tomato plants accumulate substantial amounts of this compound. As known to one skilled in the art, all higher plants produce chalconaringenin as an intermediate in flavonoid biosynthesis but only hops converts chalconaringenin to xanthohumol via prenylation and methylation reactions. Using OMT1 in other plants may make it possible to engineer xanthohumol biosynthesis in these other plants.

In other embodiments, there is provided an isolated or purified DNA molecule comprising or having at least 85%, at least 86%, at least 87%, at least 88%, at least 89%, at least 90%, at least 91%, at least 92%, at least 93%, at lest 84%, at least 95%, at least 96%, at least 97%, at least 98% or at least 99% identity to the antisense of SEQ ID No. 1 or SEQ ID No. 3. As discussed below, such antisense probes can be used to reduce expression of OMT1 and/or OMT2 in a plant of interest which would in turn for example block xanthohumol biosynthesis and result in the accumulation desmethylxanthohumol. As will be known to one of skill in the art, suitable antisense or RNA interference (RNAi) vectors are known in the art and typically an antisense or RNAi probe corresponding to a highly conserved region of the mRNA to be inhibited is selected. The length of the antisense or RNAi probe may be for example 15-100 or 15-50 nucleotides or any other suitable length known in the art.

For example, the antisense or RNAi probe may be used to block or reduce xanthohumol biosynthesis in hops so that desmethylxanthohumol accumulates which in turn provides material for synthesis of 6- and 8-prenylnaringenin.

In other embodiments, OMT1 and/or OMT2 as described above may be used to transform other organisms, for example, microorganisms such as yeast or bacteria for engineering xanthohumol biosynthesis in these organisms. It is noted that flavonoid biosynthesis has previously been transferred to yeasts (Jiang et al. 2005).

Lupulin glands were purified from cones of the hops varieties 'Taurus' and 'Nugget' and total RNA extracted from such glands. The RNA isolation procedure involved a combination of lysis in phenol-chloroform and subsequent purification using ion-exchange columns (Qiagen RNeasy). High-titre cDNA libraries were constructed using a SMART cDNA library synthesis kit (Clontech) or a cDNA library synthesis kit (Stratagene). Libraries contained a high number of recombinant clones; average cDNA length was >0.8 kb. Sequencing was performed by coring individual phage plaques and amplifying the cDNA insert by PCR or by picking bacterial colonies and amplifying plasmid template using TempliPhi (Amersham Biosciences). Purified PCR products or TempliPhi reactions were sequenced using Applied Biosystems BigDye chemistry. In total 10581 EST sequences were obtained and compared to the NCBI non-redundant (nr) database using the BLASTX algorithm. Of the 10581 ESTs, 39 showed similarity to O-methyltransferases that were predicted to encode OMTs that methylate small molecules such as secondary metabolites. These 39 sequences clustered into five groups and two singletons with group 1 containing thirteen members. The cDNA corresponding to group 1, termed HIOMT1, was full-length.

*Humulus lupulus* HIOMT1 (SEQ ID NO. 1)

```
GGACACAATTCAATCTATTTTACCCAAAAAATAACTAAGAAAGACCAATA

TGGAATCTCTAAGAGGCCAAGAACAGATATGGCAACTCATGTTCAGCTTT

GTCGACTCCATGGCCTTGAAATGCGCCATCGAGCTTCGCATTGCTGACAT

CATTCACTCTCATGGCAAACCTATAACTCTCTCCCAAATAGCTTCTGGCA

TTCGATCAAACTCCAACTCCTCCATATCTCCGAATATTCCTTACCTCTCT

CGCATCATGAGATTTCTTGTTCGAAAGAATATCTTCACTGAACATCAAGA

AGATAATGATGAGGTGATCTCATTGTACGGGCTAAGTGATAGCTCGAGAT

GGCTGTTGCGGGATTTTAAGTCAAGCCTGGCTCCCATGGTGCTCATGCAG

ACTCATCCATTGTCGATGGCGGTGTGGCATTTCCTTGAGGATTATGTGAG

AAACAGCAGCAACACTTTCGAAAAGGCTCACGGTTGTAACATTTGGGAGT

TTTCCTCAGCCAATCCAGATTTCAACAAGATCTTCAACAATGCCATGGCG

AGTATTGTGCCAATATACATGGGGGCTGTGCTTTCAAGTTATAAGGATGG

TCTTGGTTGTATTAAAGGAACAGTGGTGGACGTTGGGGGTGGTACGGGCG

GCTCCATATCAGAGCTTATGAAATATTATCCAAACATCAAAGGGATTAAC

TTTGACCTGCCACATGTGATTGCCACAGCACCGGCATTGGATGGTGTTAC

CCATATTAGTGGTGACATATTCGAGTCAATTCCTAGTGCTGATGCGGTTT

TAATGAAGGGTGTACTACATTGCTTCAGCGATGAAAAATGTGTAAAAGTA

TTGAGAAATTGTCGAAAAGCAATAACAGACAAAAAGAATGGGAAGATTAT

CATTTTGGAGATTGTGTTGGACCCAACCAGCAATCAAATATTTGACGAGA

CTCGAATGGTGTACGATTTATTGATTCCAYTCTTTAGTGGTGGAAAAGAG

AGAACTGAGCTTGAATGGAAAAGGCTATTAAACGAGGCTGGTTTTACTTC

TATCAAAATCACCAAAATTCCAATTATACCTGCTATTATTGAGGCCTTTC

TAGTGTGACAACATCGATCTATCTATATATATATAAACTAGGTTATGTTG

CTTTCAACAATAAGTTCCCTATGTACTGTTACGGTTATGTATGGTTTGCT

GTGATTAATATAATATGTTGGCAAAAAAAAAAAAAAAAA
```

The corresponding amino acid sequence of the open reading frame of HIOMT1 (SEQ ID NO. 2) is:

```
MESLRGQEQIWQLMFSFVDSMALKCAIELRIADIIHSHGKPITLSQIASG
IRSNSNSSISPNIPYLSRIMRFLVRKNIFTEHQEDNDEVISLYGLSDSSR
WLLRDFKSSLAPMVLMQTHPLSMAVWHFLEDYVRNSSNTFEKAHGCNIWE
FSSANPDFNKIFNNAMASIVPIYMGAVLSSYKDGLGCIKGTVVDVGGGTG
GSISELMKYYPNIKGINFDLPHVIATAPALDGVTHISGDIFESIPSADAV
LMKGVLHCFSDEKCVKVLRNCRKAITDKKNGKIIILEIVLDPTSNQIFDE
TRMVYDLLIPXFSGGKERTELEWKRLLNEAGFTSIKITKIPIIPAIIEAF
LV.
```

The full-length cDNA corresponding to a singleton, termed HIOMT2 (SEQ ID NO. 3), was obtained by RACE PCR using a GeneRacer kit (Invitrogen). The DNA sequence of the full-length cDNA clone of HIOMT2 is as follows:

```
ATCAATCATTCGACCTTTCTATAACATAAAAAGAAAAAGAAAAAAAGTG
AGATTAGTGTAAATGGAGTTGGCACGGAATGATCAAACCGAGGCAGCTCT
AAGAGGTGAAGCGAACGTATGGAAAAGCATTAATGGAATAGCAGATTTCA
TGGTCATGAAATGCGCCTTAGAGTTGAGAATCCCTGATATCGTACACTCG
CACTCCGCCCAATCACTTTGGCCCAAATTGCTTCTTCTGTTCCAGATTC
TCCCTCTCTGAACCTCTCCTACCTATCTCGCATCATGCGTCTACTTGTAC
GTCGTAAGATATTCTCTCAACACAAATCACTAGACGGTGAAGAAGTTCTC
TACGGGCCTACTCACTCATCTAGGTTGCTCTTAAGCAAAACTACGTTGCC
GGATCAGGTAACTTTGGCTCCGTTTGTTGCATTCATGACCCATCCCTACT
TGTCGGCTCCATGGAGCTGCTTGGCCAGGTGTGTCAAAGAAGGCGGCAAC
GGTTTTGAGATGGTCCACGGCGGCCGCCAATTATGGGACTTGTCTCCAGG
GAATCCGGAGTTCAACAAGGTTTTCAACGATGGCATGGCGAGCACGGCCA
GAATAACAACGATGGCAATTTTGTCCGAATACAGAGATGTCTTTTGTGGG
ATCTGTTCTTTGGTCGACGTCGGTGGTGAGTTTGGCGGCTCAATATCTGC
GATTGTGAAATCTCATCCGCACATAAAAGGCATCAACTATGATCTACCCC
ATGTTGTCGCCACCGCTCCAACGTACACCGGACTAGTGTCCCATGTTGGT
GGTAACATGTTTGAATGGATCCCCACTGCCGTTGCAGTTTTCATGAAGTG
GATACTTCACGATTGGGCCGATGAAGATTGTGTGAAGATCTTGAAAAATT
GTAGAAGAGCAATGCCTGAGAAGGGTGGAAAAATTATCATAGTTGACATA
GTTTTGGAGCCAGAGGGCAATGGGTTATTTGATGATGCAGCTGTGATGCT
CGATATTGCACTAATGGCACTAACACGTGGAAAGGAGAGAACCGAGAAGG
AGTGGAAGAGGGTGTTGGAAGAAGGAGGTTTCCCTCGCTACCAAATCCTC
AAAATTCCAGCTTTAACATCTGTCATTGAAGCCTATCCACAATGATCATC
ACTGTATACCTACCCTATTATGATGTTCTAGTAGTTCATAGACACTTTCT
TAAAGGTGCAATATGGATGAATAAGTTAATTATATTTAAAATAATATGAT
ATCTCCTATATATAATAAATGGCTATGGAATGGAAAATTGATAGTTTAAT
GGAAAAAAAAAA
```

The corresponding amino acid sequence of the open reading frame of HIOMT2 (SEQ ID NO. 4) is:

```
MELARNDQTEAALRGEANVWKSINGIADFMVMKCALELRIPDIVHSHSAP
ITLAQIASSVPDSPSLNLSYLSRIMRLLVRRKIFSQHKSLDGEEVLYGPT
HSSRLLLSKTTLPDQVTLAPFVAFMTHPYLSAPWSCLARCVKEGGNGFEM
VHGGRQLWDLSPGNPEFNKVFNDGMASTARITTMAILSEYRDVFCGICSL
VDVGGEFGGSISAIVKSHPHIKGINYDLPHVVATAPTYTGLVSHVGGNMF
EWIPTAVAVFMKWILHDWADEDCVKILKNCRRAMPEKGGKIIIVDIVLEP
EGNGLFDDAAVMLDIALMALTRGKERTEKEWKRVLEEGGFPRYQILKIPA
LTSVIEAYPQ.
```

The open reading frame of each enzyme was cloned into the baculovirus expression vector pFastBacHT (Invitrogen) and the resulting bacmid generated using the Bac-to-Bac system (Invitrogen). The bacmid was used to transfect *Spodoptera frugiperda* (Sf9) insect cells. After amplification of the baculovirus through several passages, insect cell monolayers were infected, cultivated for 2-4 days and then centrifuged to separate cells from culture media. Cell pellets were lysed and aliquots used directly in enzyme assay containing $^{14}$C—S-adenosyl methionine ($^{14}$C-SAM) as a methyl donor and various phenolic and phenylpropanoid natural products as substrates. Methylation activity was measured by the extraction of the enzyme reaction with ethyl acetate and its analysis by scintillation counting. In this assay, $^{14}$C-methylation of one of the proffered substrates is indicated by the presence of radioactivity in the ethyl acetate extract.

The commercial applications could come from the use of the genes to increase xanthohumol levels in hops, or to block xanthohumol biosynthesis and accumulate desmethylxanthohumol. They may also have utility as biocatalytic tools for methylation of other natural products.

REFERENCES

1. Stevens J F, Page J E (2004) Xanthohumol and related prenylflavonoids from hops and beer: to your good health! Phytochemistry 65: 1317-1330
2. Matousek J, Novak P, Briza J, Patzak J, Niedermeierova H (2002) Cloning and characterisation of chs-specific DNA and cDNA sequences from hop (*Humulus lupulus* L.). Plant Science 162: 1007-1018
3. Stevens J F, Ivancic M, Hsu V, Deinzer M L (1997) Prenylflavonoids from *Humulus lupulus*. Phytochemistry 44: 1575-1585
4. Maxwell C A, Harrison M J, Dixon R A (1993) Molecular characterization and expression of alfalfa isoliquiritigenin 2'-O-methyltransferase, an enzyme specifically involved in the biosynthesis of an inducer of *Rhizobium meliloti* nodulation genes. Plant Journal 4: 971-981
5. Zubieta C, He X Z, Dixon R A, Noel J P (2001) Structures of two natural product methyltransferases reveal the basis for substrate specificity in plant O-methyltransferases. Nat Struct Biol 8: 271-279
6. Jiang H, Wood K V, Morgan J A (2005) Metabolic engineering of the phenylpropanoid pathway in *Saccharomyces cerevisiae*. Applied and Environmental Microbiology 71: 2962-9.

The invention claimed is:

1. A purified or isolated O-methyltransferase comprising at least 95% identity to the amino acid sequence as set forth in SEQ ID No. 2.

2. A method of producing xanthohumol comprising methylating desmethylxanthohumol in the presence of the O-methyltransferase as defined in claim 1.

* * * * *